United States Patent [19]

Sagalowsky

[11] Patent Number: 4,572,211
[45] Date of Patent: Feb. 25, 1986

[54] PENILE TUMESCENCE MONITOR

[75] Inventor: Ronald L. Sagalowsky, Indianapolis, Ind.

[73] Assignee: Biorem, Inc., Indianapolis, Ind.

[21] Appl. No.: 371,611

[22] Filed: Apr. 26, 1982

[51] Int. Cl.⁴ .......................... A61B 5/10; G01D 9/00; G08B 13/18
[52] U.S. Cl. ............................ 128/774; 346/33 ME; 340/653
[58] Field of Search .............. 128/694, 774, 711, 721, 128/900, 782; 346/33 ME; 340/652, 653

[56] References Cited

U.S. PATENT DOCUMENTS

| | | | |
|---|---|---|---|
| 3,293,608 | 12/1966 | Klein et al. | 360/32 X |
| 3,651,280 | 3/1972 | Streckmann | 360/32 |
| 3,934,267 | 1/1976 | Kosaka et al. | 128/711 X |
| 4,103,678 | 8/1978 | Karwacan et al. | 128/774 |
| 4,240,440 | 12/1980 | Virgulto et al. | 128/721 |

OTHER PUBLICATIONS

Patel et al., Med & Biol. Eng & Comput, vol. 17, No. 4, Jul. 1979, pp. 460-464.

Primary Examiner—Kyle L. Howell
Assistant Examiner—John C. Hanley
Attorney, Agent, or Firm—Woodard, Weikart, Emhardt & Naughton

[57] ABSTRACT

A penile tumescence monitoring device and method which use strain gauges connected to a connector device which translates the strain gauge input into a magnetically recordable output signal. A magnetic tape recorder is used for tape recording the monitored penile tumescence. The system further includes test switches and indicating lights for testing the proper functioning of the electronic circuitry and strain gauges involved in the system.

8 Claims, 3 Drawing Figures

PENILE TUMESCENCE MONITOR

BACKGROUND OF THE INVENTION

1. Field of the Invention

This invention relates in general to a process and device for penile tumescence monitoring and, more particularly, to a device which will allow for small changes in penile circumference to be recorded on magnetic tape.

2. Description of the Prior Art

Penile tumescence monitoring is done for the purpose of medically determining whether male impotence is primarily due to physiological or psychological reasons. The monitoring involves the monitoring of the circumference of the patient's penis while he is asleep so as to determine whether the patient achieves an erection. It has been previously shown that erections will normally occur during the alpha rhythm portion of rapid eye movement portion of sleep. This monitoring aids the doctor in determining the etiology of the patient's impotence. If the patient is impotent because of physiological reasons, he will not achieve an erection while he is asleep. If the patient is impotent because of primarily psychological reasons, he will most likely achieve an erection while he is asleep. Therefore, in the situations where the patient's impotence is caused because of psychological reasons as opposed to physiological reasons a penile tumescence monitoring study may save the patient from undergoing an unnecessary operation, and hopefully encourage him to seek psychiatric counseling.

In the prior art, the penile tumescence monitors that were used tended to be large, bulky, expensive, and complicated. This meant that when a patient underwent a penile tumescence monitoring study he often had to be admitted to the hospital and spend several days there. The prior art basically used devices which used penile tumescence sensors which were attached to the patient's penis. These sensors then sent signals to a large chart recorder device which monitored the patient's penile tumescence during the evening while he slept. The fact that the patient had to check in at the hospital for the purpose of this study made the test expensive for the patient. Further the patient had to undergo a loss of privacy and in some cases much embarrassment.

Unlike the prior art, the present invention provides for a penile tumescence monitoring process and device which is small, compact, reliable and relatively inexpensive. Because the present invention is portable and easy to use the patient can take the monitor home with him and use it in the privacy of his own home while he is asleep. Thus, the patient saves the expense of a hospital stay and is assured privacy and avoids embarrassment.

The patient, in the privacy of his own home, can easily attach the sensors of the small system before he goes to sleep. The small system makes a tape recording of the patient's penile tumescence. The patient then takes this tape recording to the doctor the next day. The doctor can then play back the recording on any suitable display device, for example a large chart recorder, and from this the doctor can determine whether the patient achieved an erection while he was asleep the previous evening. Further, because it is a magnetic tape recording the doctor can alter the gain and frequency of the output so that he can easily create charts whch are easy to read and informative. In the prior art, the doctor had to work with the written chart that had been produced and if it was difficult to discern he would have to rerun the test. With a magnetic tape recording the doctor can make many charts with various resolutions without having to rerun the test and cause concern and embarrassment for the patient.

The following are examples of tumescence monitors that are found in the prior art and that are presently on the market. The Browne Corporation 7600 is a wall plug in model which records penile tumescence by use of a heat stylus on thermal-sensitive and pressure-sensitive chart paper. The Event Systems PTM-1 tumescence monitor is a battery operated device which records the tumescence by use of an impact styli on pressure sensitive chart paper. This device employs two separate styli for base and tip penile tumescence recording. The Farrall Instruments SP-30N tumescence monitor is a battery operated device which records by heat stylus on thermal sensitive chart paper. The Medical Monitoring Systems PRS-102 device is a wall plug in unit which records penile tumescence by heat styli on thermal sensitive Z-fold chart paper. It has two separate channels and styli. All of these devices tend to be expensive and fairly complicated. Further, unlike the present invention, these prior art devices have more that can go wrong with them in operation during a penile tumescence monitoring. The use of chart paper and styli can result in graphs which are difficult to read. The paper can snag. The use of heat sensitive paper and styli can result in problems if there are some variations in heat or otherwise and in general these devices tend to be less reliable and if they break down during the night when the patient is sleeping this means that the patient has to rerun the test. The present invention employs simple magnetic tape recording which is more trouble free than the chart recorders of the prior art.

These prior art devices also present the problem that if the chart recorder's graph is not easily read by the doctor the next day the patient must rerun the test so that a new chart can be made. The magnetic tape recording of the present invention is also superior because it allows the doctor to create a readable chart by playing back the magnetic tape recording. He can create charts which are easy to read by simply altering the gain and the frequency of the output. Therefore the patient does not need to rerun the test for the doctor to have a readable chart.

All of these devices use more than one strain gauge and therefore must record simultaneously the signals from the various strain gauges. The chart recorders record the signals in the various strain gauges through the use of more than one styli so that more than one line is made on the chart. The use of a magnetic tape recording allows the doctor to select to either simultaneously or individually play back both signals. Thus he can create a chart with chart lines showing the signals from both strain gauges or a chart of the signals independently and therefore the present invention provides for greater versatility. Further when the styli are used to record the signals simultaneously a problem can occur if something goes wrong with one styli and not the other and once again the test would have to be rerun. It is clear that the use of a magnetic tape recording as opposed to chart recording during a penile tumescence monitoring test ensures that the test results will be more reliably recorded and thus reduces the possibility of having the patient undergo the strain and embarrassment of another penile tumescence test.

Examples of other possible prior art devices and processes are shown in the following patents: U.S. Pat. No. 3,417,743, issued to Carrera on Dec. 24, 1968; U.S. Pat. No. 2,976,865, issued to Shipley on Mar. 28, 1961; U.S. Pat. No. 3,986,254, issued to Nordstrom on Oct. 19, 1976; U.S. Pat. No. 4,173,971, issued to Karz on Nov. 13, 1979; U.S. Pat. No. 3,461,863, issued to Sullinger on Aug. 19, 1969; U.S. Pat. No. 4,183,354, issued to Sibley et al. on Jan. 15, 1980; U.S. Pat. No. 3,845,760, issued to Birman on Nov. 5, 1974; U.S. Pat. No. 3,773,040, issued to Gavrilovich on Nov. 20, 1973 and U.S. Pat. No. 3,900,023, issued to McBride on Aug. 19, 1975.

The Carrera patent discloses an apparatus that is shaped to fit over the male penis. The apparatus has a plurality of pressure sensing devices and recording equipment. It is clear however that the device is used for enhancing sexual performance during sexual intercourse as opposed to penile tumescence monitoring. The Shipley patent discloses a cylindrical strain gauge while the Nordstrom patent shows an encased strain gauge. The Karz and Sibley patents relate to ambulatory electrocardiograph recorders. These patents and the others mentioned do not show any devices or systems which can be used for penile tumescence monitoring.

SUMMARY OF THE INVENTION

Briefly described in one aspect of the present invention there is provided a device for monitoring penile tumescence. Such device consists of a small housing which has strain gauge input jacks and magnetic tape recorder output jacks. The housing contains electronic conversion means which are engaged with both the strain gauge input jacks and the output jacks. The electronic conversion means are operable to convert strain gauge input of penile tumescence to an electronic magnetically recordable penile tumescence output signal. In a related aspect there is provided a monitoring apparatus which includes a magnetic recording means. A method for monitoring penile tumescence is also provided.

It is an object of this invention to provide an improved device to be used in penile tumescence monitoring which is portable, inexpensive and simple to use.

It is a further object of this invention to provide an improved penile tumescence monitoring apparatus which magnetically tape records the penile tumescence that is monitored, and while thereby has additional advantages such as the flexibility of replaying the magnetic tape in various modes to produce different types of print outs.

It is further an object of this invention to provide for an improved method for penile tumescence monitoring.

Related objects and advantages will become apparent as the description proceeds.

BRIEF DESCRIPTION OF THE DRAWINGS

FIG. 1 is a front, elevational view of a preferred embodiment of the connector of the present invention and the penile tumescence monitoring system it is used in.

DESCRIPTION OF THE PREFERRED EMBODIMENT

Figure 1:
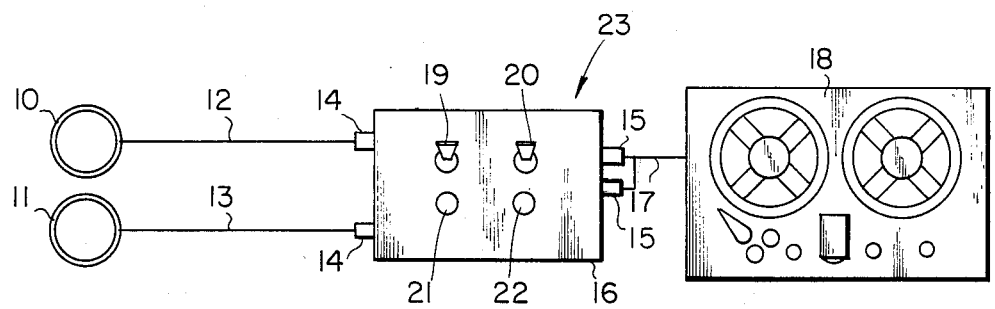

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1 there is shown a penile tumescence recording system 23. This system comprises a small housing box 16 which has strain gauge input jacks 14 and magnetic tape recorder output jacks 15. The system is very portable because the housing box and the gauges and the recorder are small and lightweight.

Figure 3:
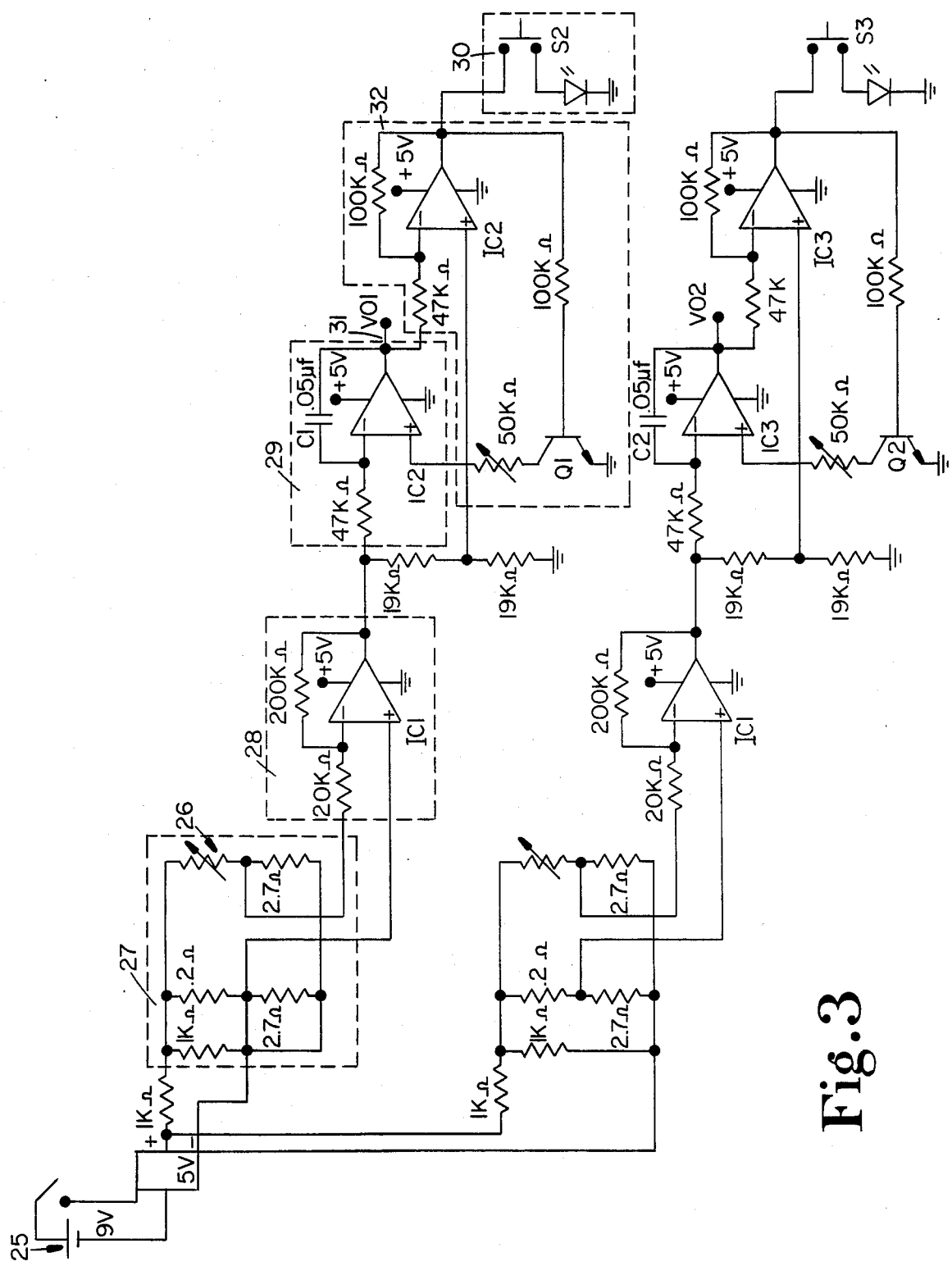
FIG. 3 is a schematic of the electronic conversion means of the preferred embodiment.

The housing box 16 contains electronic conversion means, as shown in FIG. 3, which are electrically connected to the input jacks 14 and electrically connected to the output jacks 15. The housing box 16 further has circuit testing means for testing the functioning of the electronic conversion means. Circuit testing control means are provided for controlling the circuit testing means for testing of the electronic conversion means for proper functioning. The control means are preferably switches including a tip strain gauge circuitry test switch 19 and base strain gauge circuitry test switch 20. Circuit testing indicator means for indicating the results of the test are adjacent to these switches and these are preferably a tip switch light 21 and a base switch light 22.

One of the input jacks 14 on the housing box 16 is connected by input cable 12 with the base strain gauge 10 which is to be mounted to the base of the patient's penis. The other input jack 14 on the housing box 16 is connected by input cable 13 to tip strain gauge 11 which is to be mounted to the tip of the patient's penis just below the glans. The output jacks 15 on the housing box 16 is connected to a magnetic tape recorder 18 by output cable 17.

Figure 2:
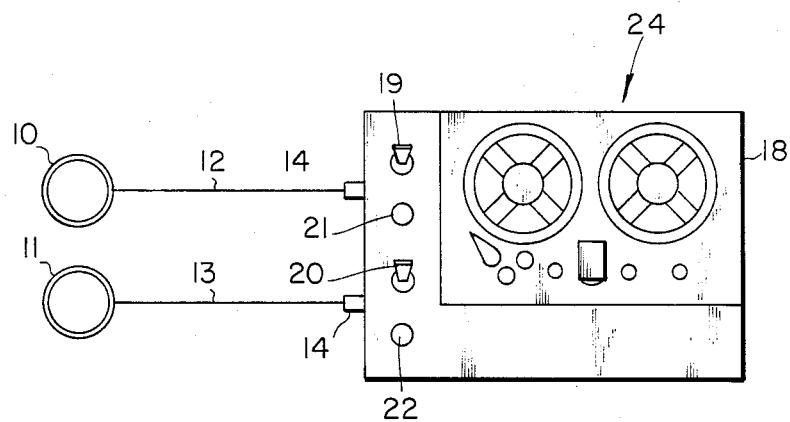
FIG. 2 is a front, elevational view of the apparatus which contains the connector and the recorder means for a penile tumescence monitoring system.

FIG. 2 shows a combined connector and recorder apparatus 24. The combined connector and recorder apparatus 24 is a single unit which contains a magnetic tape recorder 18. The apparatus also has strain gauge input jacks 14 which connect to the base strain gauge 10 by cable 12 and to the tip strain gauge 11 by cable 13. The combined connector recorder apparatus 24 also has testing switches which are tip test switch 19 and base test switch 20. Each switch has an adjacent light being a tip switch light 21 adjacent to the tip test switch 19 and base switch light 22 adjacent to the base test switch 20.

In the preferred embodiment the strain gauges are mercury strain gauges which are a length of highly elastic tubing filled with mercury. However, the term strain gauge as used herein is intended to include any device suitable for providing an indication of the size of the penis in terms of an electrical signal. Contact is made to the ends of the mercury column by means of wires inserted in the ends of the tubing. As the tubing is stretched, the enclosed mercury column is lengthened and narrowed, increasing its electrical resistance. When tension is removed, the gauge returns to its original length. The resistance increases linearly with the length when the length changes are small compared to the unstretched length. These gauges, as represented by strain gauges 10 and 11, are preferably placed around the base of the patient's penis and at the tip of the patient's penis just behind the glans. As the patient sleeps, if he achieves an erection the strain gauges lengthen and the mercury resistance increases. This is converted by the electrical circuitry within the housing box 16 into an output signal which is magnetically recorded on tape recorder 18.

The system provides for testing of the electrical circuitry through the uses of the tip test switch 19 and its adjacent light 21 and base test switch 20 and its adjacent light 22. This testing allows the patient to test the system so that he is sure that it is working properly and that he has connected the strain gauges properly to the wheatstone bridge circuit 27 for example. When the tip test switch 19 is pressed, the tip test light 21 will assume one of three states depending upon the function or malfunction of the electrical circuitry which is connected with the strain gauge mounted to the tip of the patient's penis. If the circuitry for the tip strain gauge is functioning properly, the tip test light 21 will remain steadily illuminated as the tip test switch 19 is pressed when the tip strain gauge 10 (resistor 26) has not yet been mounted to the wheatstone bridge circuit 27. If the tip strain gauge 10 is functioning properly and mounted properly to the wheatstone bridge circuit 27, the tip test light 21 will flash when tip test switch 19 is pressed. If tip test switch 19 is pressed and tip test light 21 neither goes on or flashes, this is an indication that either the circuitry or the battery that powers the electrical circuitry in the housing box 16 is malfunctioning. The base test switch and base switch light work in the same manner for the purposes of testing the base strain gauge 11 and the electrical circuitry which corresponds to the base strain gauge 11.

FIG. 3 illustrates the electronic conversion means comprising internal electrical circuitry in housing box 16 which converts the strain gauge measurements to a magnetically recordable output signal. The output signals from each strain gauge are simultaneously recorded as is known in the art so that the recording can be replayed and an output for each strain gauge could be made on, for example, a chart maker device. The disclosed electrical configuration is the preferred embodiment. There may be other electrical configurations possible which will achieve the same results and these configurations are encompassed by the spirit of the present invention.

The circuitry used in the preferred embodiment in connection with the tip strain gauge and the base strain gauge is identical and therefore only one strain gauge circuit path need be fully explained. A nine volt battery 25 is used to provide the electrical power for this circuitry. The strain gauge is incorporated as an electrical resistor 26 into an unbalanced Wheatstone bridge circuit 27, the output of which is a DC voltage linearly related to the change in resistance of the strain gauge 26. This voltage is amplified and impedance-matched through a buffer stage 28 to a circuit 29 and output feedback loop circuit 32 whose AC output frequency 31 is proportional to the DC input voltage from circuit 28. The AC output 31 may then be recorded on magnetic tape using a standard AC coupled audio tape recorder 18. The recorder, preferably, should have a sufficiently slow tape speed so as to provide extended record time so that the patient need not wake up to change the recording tape. The preferred embodiment uses an American Edwards model 2500 Holter recorder which is extremely portable and easy to use with the connector system of the preferred embodiment. These recorders are reliable and provide all of the advantages in reliability and ease of use that magnetic tape recording provides over the prior art chart making devices which need styli and various forms of chart paper. It is again pointed out that an electronically recorded signal is more versatile in later producing charts than the making of a possibly difficult to read chart at the time of the test.

The circuit testing means includes circuitry for the circuit testing control and indicator means. In the preferred embodiment the circuitry for the testing control switches and indicator lights has a switch and diode circuit 30 which corresponds to a test switch and its adjacent test switch light. For example, the switch S2 in FIG. 3 corresponds to test switch 19 and the diode of circuit 30 corresponds to test light 21. This testing control and indicator circuitry 30 is engaged with the output circuitry 29 and 32 so as to test the output for proper functioning. As is apparent from the circuit of FIG. 3, the electrical connection between test circuit 30 and output circuits 29 and 32 is such that a frequency output is received by test circuit 30 from circuit 32. As previously described, the test light diode of circuit 30 responds in one of three manners when the switch S2 (test switch 19) is engaged to complete electrical connection between the diode of circuit 30 and output circuit 32 as shown in FIG. 3. The diode either flashes, remains steadily illuminated or does not light. When the diode does not light it means that the diode is not receiving electrical current from circuit 32 which means that either the electrical conversion means of FIG. 3 is malfunctioning or the power source 25 is malfunctioning. When strain gauge 26 is not yet connected to wheatstone bridge circuit 27 the frequency output of output circuits 29 and 32 would be very large if the electrical conversion means and the power source are functioning. This very high frequency output would result in the apparent steady illumination of the diode of test circuit 30 when the test switch S2 is engaged. If the patient has properly mounted strain gauge 26 to circuit 27 there would be a resulting frequency output from circuit 32 to the diode of circuit 30 when the test switch S2 is engaged. This frequency output would cause the diode to flash. When the strain gauge 26 is stretched its electrical resistance increases. It being easily understood from the circuit of FIG. 3, this would be proportionately translated by the output circuits 29 and 32 into a higher frequency output and the diode would flash at a greater rate when the test switch S2 is engaged. Consequently, the user can test for malfunctions in the power source or the electrical conversion means by determining if the diode is lighting at all when he engages the test switch. He can then test to see if he has properly mounted the strain gauge 26 to the wheatstone bridge circuit 27. If he has, the diode will flash and if he has not then the diode will remain steadily illuminated. The disclosed electrical configuration for the circuit testing means is one embodiment and while there may be other configurations which will achieve the same results these are encompassed by the spirit of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A connector device for connecting a penile strain gauge adapted to send penile strain gauge input signals of penile tumescence with a magnetic recording device for the purpose of recording penile tumescence, said device comprising:

a small housing;

strain gauge input jack means mounted to said small housing for connecting with a penile strain gauge;

magnetic recorder output jack means mounted to said small housing for connecting with a magnetic recording device;

electronic conversion means electrically connected with said input jack means and said output jack means and said electronic conversion means for receiving penile strain gauge input signals of penile tumescence at said input jack means and converting said penile strain gauge input signals to electronic magnetically recordable penile tumescence output signals at said output jack means, said conversion means being mounted in said small housing; and circuit testing means electrically connected with said electronic conversion means, said circuit testing means being operable to test said electronic conversion means to determine whether said electronic conversion means (1) is receiving electrical power, and (2) is converting input signals at said input jack means to output signals at said output jack means, or (3) is receiving penile strain gauge input signals at said input jack means from a penile strain gauge connected to said input jack means.

2. The connector of claim 1 wherein said circuit testing means includes (1) circuit testing control means and (2) circuit testing indicator means; said control means being operable to control said test of the electronic conversion means, said indicator means being operable to indicate whether said electronic conversion means (1) is receiving electrical power, (2) is converting input signals at said input jack means to output signals at said output jack means when a strain gauge is not connected to said input jack means, or (3) is receiving penile strain gauge input signals at said input jack means from a penile strain gauge connected to said input jack means and is converting said input signals to said output signals at said output jack means.

3. The connector of claim 2 wherein said circuit testing control means includes switches mounted to said small housing and electrically connected to said circuit testing means, said indicator means including switch lights mounted to said small housing adjacent said switches and electrically connected to said indicator means.

4. The connector of claim 3 wherein said switches have an on state and an off state; and in which said switch lights assume one of the following states when said switches are in the on state: (1) a steady illuminated state corresponding to the receipt of electrical power by the electronic conversion means and the conversion by said electronic conversion means of input signals at said input jack means to output signals at said output jack means when a strain gauge is not connected to said input jack means, (2) a flashing state corresponding to the receipt of electrical power by the electronic conversion means and the receipt by the electronic conversion means of penile strain gauge input signals at the input jack means when a penile strain gauge is connected to said input jack means and the conversion by said electronic conversion means of said penile strain gauge input signals to said output signals at said output jack means, and (3) an off state corresponding to no electrical power being received by said circuit testing means.

5. An apparatus for recording penile tumescence sensed by strain gauges adapted to send penile strain gauge input signals of penile tumescence, said apparatus comprising:

a small housing;

strain gauge input jack means mounted to said small housing for connecting with said penile strain gauges and receiving said strain gauge input signals from said strain gauges;

magnetic recording means mounted in said small housing for magnetically recording electronic penile tumescence output signals received at a recording input;

electronic conversion means electrically connected with said input jack means and the recording input of said recording means and said electronic conversion means being for receiving said strain gauge input signals of penile tumescence at said input jack means and converting said strain gauge input signal to electronic magnetically recordable penile tumescence output signals, said electronic conversion means further being for providing said output signals to the recording input of said recording means for magnetic recording thereof, said conversion means being mounted in said small housing; and circuit testing means electrically connected with said electronic conversion means, said circuit testing means being operable to test said electronic conversion means to determine whether said electronic conversion means (1) is receiving electrical power, and (2) is converting input signals at said input jack means to output signals at said output jack means, or (3) is receiving penile strain gauge input signals at said input jack means from a penile strain gauge connected to said input jack means.

6. The apparatus of claim 5 wherein said circuit testing means includes (1) circuit testing control means and (2) circuit testing indicator means; said control means being operable to control said test of the electronic conversion means, said indicator means being operable to indicate whether said electronic conversion means (1) is receiving electrical power, (2) is converting input signals at said input jack means to output signals at said output jack means when a strain gauge is not connected to said input jack means, or (3) is receiving penile strain gauge input signals at said input jack means from a penile strain gauge connected to said input jack means and is converting said input signals to said output signals at said output jack means.

7. The apparatus of claim 6 wherein said circuit testing control means includes switches mounted to said small housing and electrically connected to said circuit testing means, said indicator means including switch lights mounted to said small housing adjacent said switches and electrically connected to said indicator means.

8. The apparatus of claim 7 wherein said switches have an on state and an off state; and in which said switch lights assume one of the following states when said switches are in the on state: (1) a steady illuminated state corresponding to the receipt of electrical power by the electronic conversion means and the conversion by said electronic conversion means of input signals at said input jack means to output signals at said output jack means when a strain gauge is not connected to said input jack means, (2) a flashing state corresponding to the receipt of electrical power by the electronic conversion means and the receipt by the electronic conversion means of penile strain gauge input signals at the input jack means when a penile strain gauge is connected to said input jack means and the conversion by said electronic conversion means of said penile strain gauge input signals to said output signals at said output jack means, and (3) an off state corresponding to no electrical power being received by said circuit testing means.

* * * * *